CHRYSANTHEMUM PLANT
Filed July 30, 1974
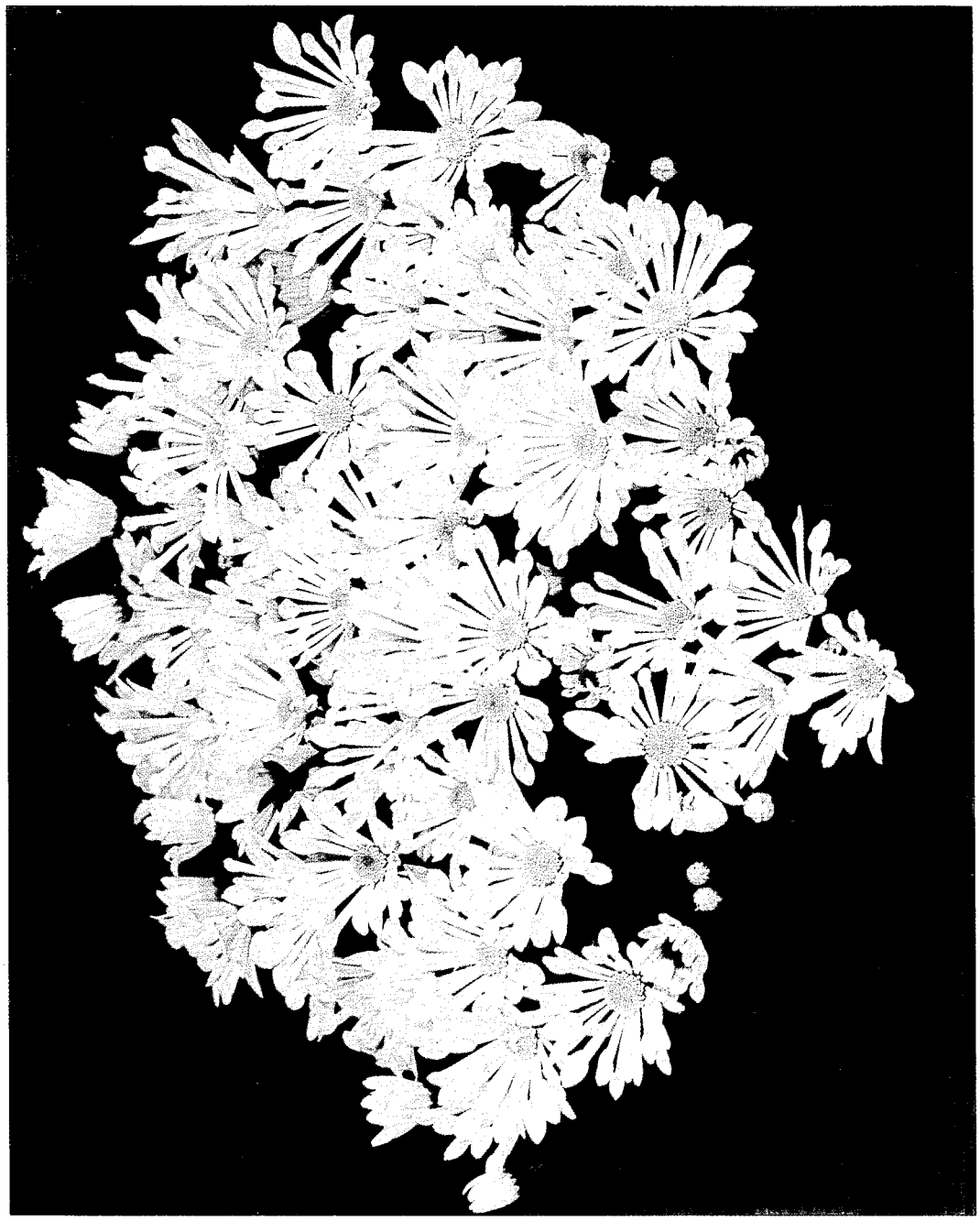

United States Patent Office

Plant Pat. 3,777

Patented Sept. 2, 1975

3,777
CHRYSANTHEMUM PLANT

Walter H. Jessel, Jr., Doylestown, and William E. Duffett, Akron, Ohio, assignors to Yoder Brothers, Inc., Barberton, Ohio

Filed July 30, 1974, Ser. No. 493,047
Int. Cl. A01h *5/00*
U.S. Cl. Plt.—74 1 Claim

The present invention comprises a new and distinct cultivar of chrysanthemum plant known by the varietal name Spice which is a seedling of #67079–001 (Dramatic, U.S. Plant Pat. No. 3,189) × #64274–006 (Sunburst Cushion, U.S. Plant Pat. No. 3,279). The numbers preceding the cultivars names are numbers used to identify the cultivars for breeding purposes.

The new cultivar is similar in many respects to Yellow Spinwheel, disclosed in U.S. Plant Pat. 3,416, issued Jan. 1, 1974. Spice has the same characteristics as Yellow Spinwheel of:

1. Use as a yellow spooned daisy for spray pot mums.
2. Vigor, spread and general growth habit.
3. Foliage color.
4. Excellent breaking action, requiring only 4 rooted cuttings per 6″ pot to produce a commercial size pot.

The new cultivar is distinguished from Yellow Spinwheel by the following characteristics when grown under comparable conditions:

1. A darker yellow flower color.
2. Flower size approximately 1″ larger in diameter.
3. The spoon tip of the petal on Spice does not turn down or reflex. The spoon tip on Yellow Spinwheel does turn down, or reflexes, which provides less form retention and tends to contribute to an aged appearance.
4. Reduced pollen development in the disc of the flower of Spice which provides improved keeping quality, up to 7 days longer bench life, and 10–14 days longer home life.
5. A different foliage shape and texture. Spice has a smoother texture with finer serrated margins and less indentation.
6. An improved uniformity of response and no vegetative growth under short days and the lower light intensities of late fall, winter and early spring.

7. A year round period of value in all areas of the United States. Yellow Spinwheel is only recommended April through December in the northern areas of the United States.
8. Improved color retention, not oxidizing or fading its color as much as Yellow Spinwheel as the flower matures.
9. Improved color clarity. Spice does not develop bronze tinging at finishing temperatures below 60° F. as is the case with Yellow Spinwheel.
10. Approximately 2–3 days earlier response.
11. Tolerates 58° F. for uniform initiation and development. Yellow Spinwheel becomes vegetative and responds unevenly at or below that temperature.

The new cultivar was selected from the progeny of the designated cross, and when asexually reproduced by cuttings at Barberton, Ohio, has been found to retain its distinctive characteristics through successive propagation.

The new cultivar, when grown in the vicinity of Barberton, Ohio, has a response period of approximately 8½ weeks.

The following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern United States, southeastern and southwestern United States, and coastal California is from January through December; southern Florida, under outdoor conditions, October through April.

The accompanying color photographic drawing shows the unique characteristics of the new cultivar, with the color being as nearly true as possible with color illustrations of this type.

In the following description, color references are made to the Munsell Book of Color, 1963 edition, and comparisons are made with the cultivar Yellow Spinwheel. Where only a single value or description appears for the new cultivar, the same value or description applies as well to the comparison cultivar Yellow Spinwheel.

Botanical classification: *Chrysanthemum morifolium*, Ramat.

| | Spice | Yellow Spinwheel |
|---|---|---|
| Bloom: | | |
| Size | 2¾″ to 3″ | 1¾″. |
| Fully expanded | 3¼″ | 2¼″. |
| Borne | Terminal clusters on elongated branches | |
| Stems | Wiry | Strong. |
| Form | Spoon (single) | |
| Permanence | 18–26 days | 10–12 days. |
| Color: | | |
| Center of flower | Yellow-green, 2.5GY7/10 to yellow, 3.75Y8/12 | Yellow, green, 2.5GY7/10 to green, 5Y8/10. |
| Base of petals | Yellow-green, 2.5GY7/10 | |
| Inside of petals | Dark yellow, 7.5Y8.5/12 to yellow, 7.5Y8.5/10 | Yellow,7.5Y8.5/12 to light yellow, 10Y9/6. |
| Reverse of petals | Yellow, 7.5Y8.5/10 | Light yellow, 10Y9/6. |
| Tonality from a distance | Golden yellow | Yellow. |
| Discoloration | Yellow, 7.5Y8.5/10 | Light yellow, 10Y9/6. |
| Petals: | | |
| Texture | Smooth | |
| Appearance and form | Tubular at base flaring last ¼″ to spoon, blunt 1–2 notched tip. | Tubular, flaring to spoon at tip, tapering to a blunt multi-notched point. |
| Arrangement | Composite, whorled on a single receptacle | |
| Persistence | Resists shatter | |
| Fragrance | Typical chrysanthemum | |
| Reproductive organs: | | |
| Stamen, anthers | 200+ | |
| Pollen | Abundant to none (functional sterility) | Abundant. |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Spreading | |
| Height | Approximately 11″–13″ in a 4-cutting, 6″ pot, grown as a spray pot given one 2,500 p.p.m. application of B–9 approximately 2 weeks after pinching, and 8 week tall treatment (1–2 weeks of long days) as defined in the timetables of Yoder Brothers, Inc., Barberton, Ohio, for the various recommended seasons. | Approximately 11″–13″ in a 4-cutting, 6″ pot, grown as a spray pot given one 2,500 p.p.m. application of B–9 approximately 2 weeks after pinching, and 9 week medium treatment (1–2 weeks of long days) as defined in the timetables of Yoder Brothers, Inc., Barberton, Ohio, for the various recommended seasons. |

| | Spice | Yellow Spinwheel |
|---|---|---|
| Spread | Approximately 8"–10" in a 4-cutting, 6" pot, grown as a spray pot given one 2,500 p.p.m. application of B-9 approximately 2 weeks after pinching and 8 week tall treatment (1–2 weeks of long days) as defined in the timetables of Yoder Brothers, Inc., Barberton, Ohio, for the various recommended seasons. | Approximately 8"–10" in a 4-cutting, 6" pot, grown as a spray pot given one 2,500 p.p.m. application of B-9 approximately 2 weeks after pinching, and 9 week medium treatment (1–2 weeks of long days) as defined in the timetables of Yoder Brothers, Inc., Barberton, Ohio, for the various recommended seasons. |
| Foliage: | | |
| Top side | Dark green, 7.5GY3/4 | |
| Size | Up to 5" in length and 2¾" in width | Up to 6½" in length and 3¾" in width. |
| Quantity | Numerous | |
| Shape | Spatulate lobed | |
| Texture | Smooth | Coarse. |
| Ribs and veins | Moderately prominent | Prominent. |
| Edge | Moderately indented | Deeply indented. |
| Serration | Finely serrated | Deeply serrated. |
| Under side | Medium green, 7.5GY5/4 | |
| Stipules | Prominent on vegetative growth to rudimentary on reproductive growth. | Rudimentary: |

We claim:

1. A new and distinct cultivar of chrysanthemum characterized particularly by its dark yellow flower color; flower size which ranges from 2¾" to 3¼" when fully expanded; its spoon petal tip which does not turn down or reflex; reduced pollen development in the disc of the flower which provides improved keeping quality; a smooth textured foliage with finely serrated margins and moderate indentation; improved uniformity of response and no vegetative growth under short days and the lower light intensities of late fall, winter and early spring; a year round period of value in all areas of the United States; improved color retention, with no oxidation or fading as the flower matures; improved color clarity, with no bronze tinging at finishing temperatures below 60° F.; a response period of approximately 8½ weeks; and by its ability to tolerate 58° F. temperature for uniform initiation and development.

No references cited.

ROBERT E. BAGWILL, Primary Examiner